United States Patent
DiFoggio et al.

(10) Patent No.: US 7,214,933 B2
(45) Date of Patent: May 8, 2007

(54) METHOD AND APPARATUS FOR A DOWNHOLE FLUORESCENCE SPECTROMETER

(75) Inventors: Rocco DiFoggio, Houston, TX (US); Arnold Walkow, Houston, TX (US); Paul Bergren, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 315 days.

(21) Appl. No.: 10/453,717

(22) Filed: Jun. 3, 2003

(65) Prior Publication Data

US 2004/0007665 A1 Jan. 15, 2004

Related U.S. Application Data

(60) Provisional application No. 60/385,633, filed on Jun. 4, 2002.

(51) Int. Cl.
*G01N 21/64* (2006.01)
*G01V 5/08* (2006.01)

(52) U.S. Cl. ................... 250/269.1; 250/255

(58) Field of Classification Search ........... 250/255, 250/256, 269.1

See application file for complete search history.

(56) References Cited

U.S. PATENT DOCUMENTS

| | | | |
|---|---|---|---|
| 5,049,738 A | | 9/1991 | Gergely et al. |
| 5,166,747 A | * | 11/1992 | Schroeder et al. .......... 356/326 |
| 5,762,419 A | * | 6/1998 | Yam .............................. 374/2 |
| 5,912,459 A | | 6/1999 | Mullins et al. |
| 5,965,896 A | * | 10/1999 | Marton .................... 250/559.4 |
| 6,008,055 A | * | 12/1999 | Zhu et al. .................... 436/172 |
| 6,016,191 A | | 1/2000 | Ramos et al. |
| 6,023,340 A | | 2/2000 | Wu et al. |
| 6,069,694 A | * | 5/2000 | VonBargen ................. 356/246 |
| 6,075,595 A | | 6/2000 | Malinen |
| 6,075,611 A | | 6/2000 | Dussan V. et al. |
| 6,140,637 A | | 10/2000 | Mullins et al. |
| 6,268,603 B1 | | 7/2001 | Mullins et al. |
| 6,321,839 B1 | | 11/2001 | Vereecken et al. |

(Continued)

FOREIGN PATENT DOCUMENTS

WO  WO 92/07249  4/1992

(Continued)

OTHER PUBLICATIONS

A.R. Smits et al., "In-Situ Optical Fluid Analysis As An Aid To Wireline Formation Sampling", SPE Formation Evaluation, Jun. 1995, pp. 91-98.

*Primary Examiner*—Albert Gagliardi
(74) *Attorney, Agent, or Firm*—Madan Mossman & Sriram PC

(57) ABSTRACT

The invention comprises an apparatus and method for simple fluorescence spectrometry in a down hole environment. The apparatus and method utilization of two UV light bulbs and an optically clear UV coupler and a fluid containment system. The optically clear UV coupler and fluid containment system are made of sapphire. The apparatus is attached in a manner that enables light transmitted from a light source on the far side of the fluid containment system to pass through a pathway in a plate holding the UV bulbs. UV light illuminates the fluid, which in turn fluoresces light. The fluoresced light is transmitted back towards the UV bulb mount and through the pathway towards an optical spectrum analyzer.

23 Claims, 3 Drawing Sheets

U.S. PATENT DOCUMENTS

| | | |
|---|---|---|
| 6,420,869 B1 | 7/2002 | DiFoggio |
| 6,476,384 B1 * | 11/2002 | Mullins et al. .......... 250/269.1 |
| 6,529,543 B1 * | 3/2003 | Anderson et al. ........... 372/108 |
| 6,678,050 B2 * | 1/2004 | Pope et al. ................. 356/435 |
| 6,704,109 B2 | 3/2004 | Wu et al. |
| 6,743,221 B1 * | 6/2004 | Hobart et al. ................... 606/4 |
| 6,768,105 B2 * | 7/2004 | Mullins et al. .......... 250/269.1 |
| 2001/0023614 A1 | 9/2001 | Tubel et al. |
| 2002/0118905 A1 | 8/2002 | Wu et al. |
| 2002/0176646 A1 | 11/2002 | Wu et al. |
| 2003/0029995 A1 | 2/2003 | Mullins et al. |
| 2004/0000636 A1 | 1/2004 | Mullins et al. |

FOREIGN PATENT DOCUMENTS

| | | |
|---|---|---|
| WO | WO 01/20322 | 3/2001 |
| WO | WO 01/20322 A1 | 3/2001 |
| WO | WO 200120322 A1 * | 3/2001 |

* cited by examiner

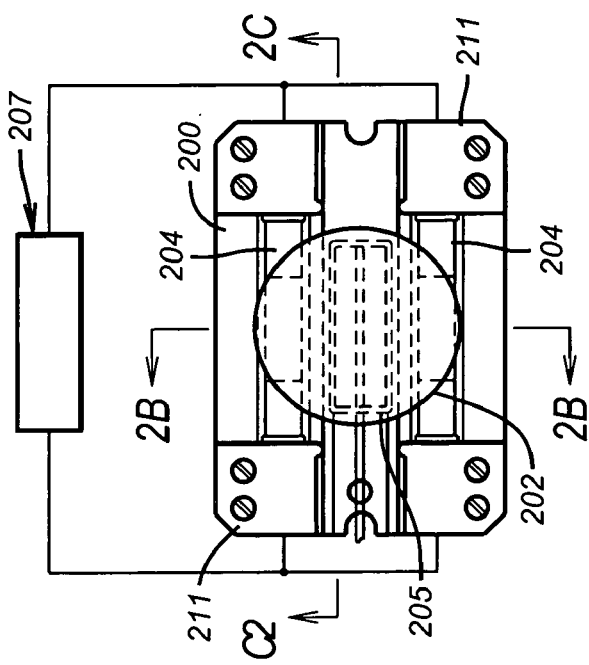
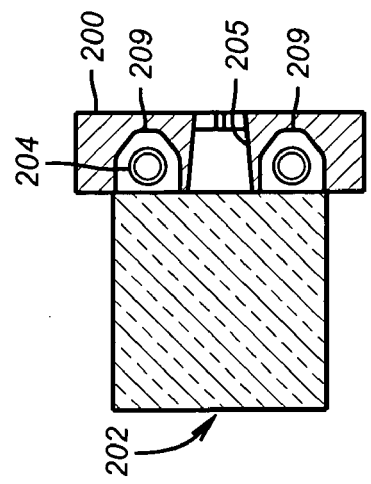
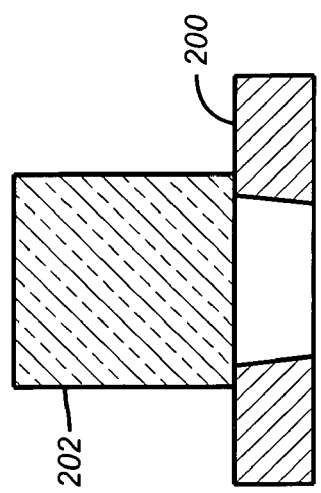
FIG. 2A
FIG. 2B
FIG. 2C

US 7,214,933 B2

METHOD AND APPARATUS FOR A DOWNHOLE FLUORESCENCE SPECTROMETER

CROSS-REFERENCE TO RELATED APPLICATIONS

This patent application takes priority from U.S. Provisional Patent Application Ser. No. 60/385,633 filed on Jun. 4, 2002 entitled "A Method and Apparatus for a Downhole Fluorescence Spectrometer" by DiFoggio et al. This application is related to U.S. Pat. No. 6,798,518, issued on Sep. 28, 2004, entitled "A Method and Apparatus for a High Resolution Downhole Spectrometer" by Rocco DiFoggio, Paul Bergen and Arnold Walkow, which is hereby incorporated herein by reference in its entirety. This application is related to U.S. Pat. No. 6,683,681, issued on Jan. 27, 2004, entitled "A Method and Apparatus for a Derivative Spectrometer" by Rocco DiFoggio, Paul Bergen and Arnold Walkow, which is hereby incorporated herein by reference in its entirety. This application is related to the U.S. patent application Ser. No. 10/119,492 filed on Apr. 10, 2002 by Rocco DiFoggio et al., entitled "A Method and Apparatus for Downhole Refractometer And Attenuated Reflectance Spectrometer" which is hereby incorporated herein by reference in its entirety.

BACKGROUND OF THE INVENTION

1. Field of the Invention

The present invention relates to an apparatus and method for performing simple fluorescence spectrometry in a down hole environment.

2. Background of the Related Art

Fluorescence analysis has been performed on cuttings or cores obtained during the drilling of wells to determine the presence of hydrocarbons in pore fluid. An example of such a technique can be found in U.S. Pat. No. 4,690,821. In techniques such as these, cuttings or cores are cleaned to remove any drilling fluid products, which might otherwise interfere with the analysis. The samples are crushed and extracted with a solvent, which is then analyzed. Alternatively the sample is irradiated directly and the fluorescence analyzed. While this technique can provide reasonably accurate analysis of the pore fluids, there are certain drawbacks. Cores are relatively expensive to obtain and must be returned to the surface for analysis. Also, since cores are only taken from specific locations, it is possible that hydrocarbon-bearing formation can be overlooked. Cuttings are obtained continuously in drilling, but have the disadvantage that it is not possible to determine at the surface exactly where the cuttings originate downhole, making the identification of hydrocarbon-bearing formations difficult. Also, cuttings give no accurate indication of the extent of any hydrocarbon bearing formations. Recent innovations have concentrated on performing fluorescence experiments in a downhole environment.

U.S. Pat. No. 5,912,459 by Mullins et al. titled Method And Apparatus For Fluorescence Logging discloses a method comprising illuminating a borehole with light from a source within a tool and detecting any fluorescent radiation with a detector in the tool and analyzing the fluorescent radiation to determine the presence of hydrocarbon in the formation. Preferably, the borehole wall is illuminated and fluorescence detected through a window in the tool which is pressed against the borehole wall. The window is typically pressed against the borehole wall with sufficient force to displace any mudcake for a substantial time, as the tool is moved through the borehole. Pressing the window against the borehole wall minimizes rugosity effects, assuming low rugosity.

PCT application (International Publication Number WO 01/20322 A1) discloses a method of fluorescence spectrometry for predicting the asphaltene precipitation onset pressure in a down hole formation. The invention of this patent comprises illuminating and measuring an isolated sample at several pressures. As asphaltenes precipitate, they induce significant optical scattering. Asphaltene precipitation is detected as a sharp reduction of transmitted light and a large increase in the light scattering strength of the sample. WO 01/20322 teaches fluorescence as a determination of contaminants only. Thus, there is a need for a method and apparatus for determining oil properties and to further oil sample purity using fluorescence.

A down hole environment is a difficult one in which to operate a sensor. Measuring instruments in a downhole environment need to work under conditions of limited space within a tool's pressure housing, at elevated temperatures, and they need to withstand shocks and vibrations. Thus, there is a need for a simple but robust fluorescence spectrometer suitable for operation in a down hole environment.

SUMMARY OF THE INVENTION

The present invention comprises an apparatus and method for performing simple fluorescence spectrometry in a down hole environment. The apparatus can be attached to a down hole fluid characterization module, that is already in use. The apparatus comprises two UV light bulbs and an optically clear UV coupler or light pipe and a fluid containment system for containing a sample under analysis. The optically clear UV coupler and fluid containment system are made of sapphire. The fluid containment system already exists as part of the Baker Atlas SampleView$^{SM}$ RCI tool. The apparatus of the present invention is attached in a manner that enables light transmitted by a light source on the far side of the fluid containment system to pass through a pathway in a plate holding the UV bulbs. UV light illuminates the fluid, which in turn fluoresces. The fluoresced light from the sample is transmitted back towards the UV bulb mount and through the light pipe pathway towards an optical spectrum analyzer for analysis.

In one embodiment of the invention, an operator monitors crude-oil sample cleanup over time by observing the rising and leveling off of a series of samples fluorescence over time. In another embodiment of the invention, an operator estimates crude oil properties from fluorescence-ratio models, which are not sensitive to dilution by a non-fluorescing liquid, such as the filtrate of synthetic mud. A processor is provided to host a chemometric equation or neural network for prediction of a fluid property based on the measured fluorescence spectrum.

A reflective surface is provided behind the UV bulbs to increase the intensity of the illuminating UV light on the sample. The optically clear UV coupler or sapphire light pipe further increases the intensity. Since the intensity of the UV bulbs is temperature-dependent, the present invention monitors this light intensity. The intensity of a red line of proportional intensity in the emission spectrum of the UV bulb is monitored using light sensing devices that are already present and in use in the Baker Atlas SampleView$^{SM}$ RCI tool. The strike voltage of the UV bulb also increases with temperature. The present invention counters this voltage creep providing an alternation of polarity between each strike.

BRIEF DESCRIPTION OF THE FIGURES

FIG. 2A–C are diagrams of the components to add this ultra-violet light source to a spectral analysis unit.

DETAILED DESCRIPTION OF A PREFERRED EMBODIMENT

Figure 1:
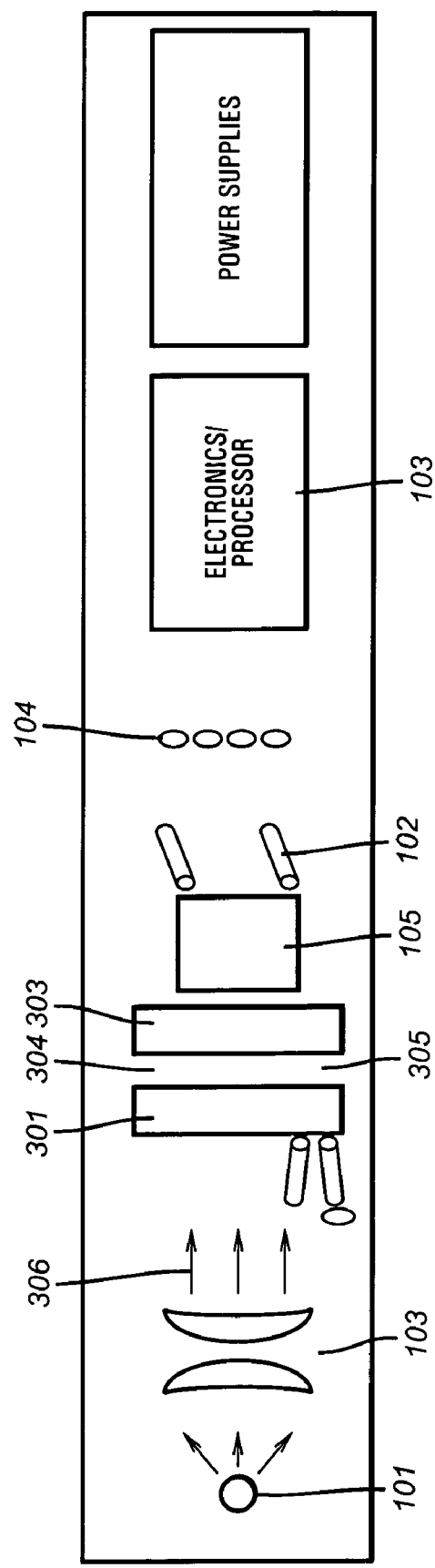
FIG. 1 is a diagram of the Fluid Characterization Module SampleView$^{SM}$.

FIG. 1 illustrates the existing space layout within a downhole fluid characterization module, as, for example, the Baker Atlas SampleView$^{SM}$ RCI tool. A UV light source 101 (e.g. tungsten light bulb) emits light toward a sample, and a collimating lens device 103 is positioned between the UV light source 102 and the sample collimates this light. The collimated light is incident generally perpendicular to a first sapphire window 301. Sapphire windows 301 and 303 lie generally perpendicular to the collimated beam of light 306 and are separated by a gap or channel 304 enabling a fluid sample 305 to flow between them. Reflected and fluoresced light can be used to determine sample properties. The existing down hole tools (FIG. 1) are fitted with a UV light source, which can be turned on when the tungsten light source 101 is turned off. A spectrometer 104, comprising single wavelength filters over photodiodes, enables collecting the crude oil fluorescence. Electronics/processor 308 acquire and process the output of the photodiodes.

FIG. 2A–C illustrate the components provided by the present invention to add a ultra-violet light source to a spectral analysis unit, such as the unit shown in FIG. 1. A base plate 200 and screws are provided which serve as a means of attachment to the spectral analysis unit (e.g., SampleView$^{SM}$). Four bulb mounts 211 comprise electrical insulating material and screws to hold the mounts in place. These same screws are used to attach the base plate 200 to the spectral analysis unit. An optically clear UV coupler 202 is shown in this diagram to show its positional relationship to two ultraviolet bulbs 204 when assembled into the system. The coupler 202 overlaps the light emitting areas of the bulbs 204, thereby confining the path of the UV light to the volumetric region of the optical coupler 202.

The rectangular window 205 in the center of the base plate 220 provides a pathway through the base plate for a reflected ultra-violet fluorescence response to pass. This pathway enables analysis of other light signals as well (such as due to the tungsten light source) when the UV bulbs 204 are turned off. A high voltage power supply 207 provides the power to turn the UV bulbs 204 on at 175° C. The UV reflectors 209 are segmented in a manner to aim the reflected light at an angle that will efficiently confine the light within the optically clear UV coupler 202.

Figure 3:
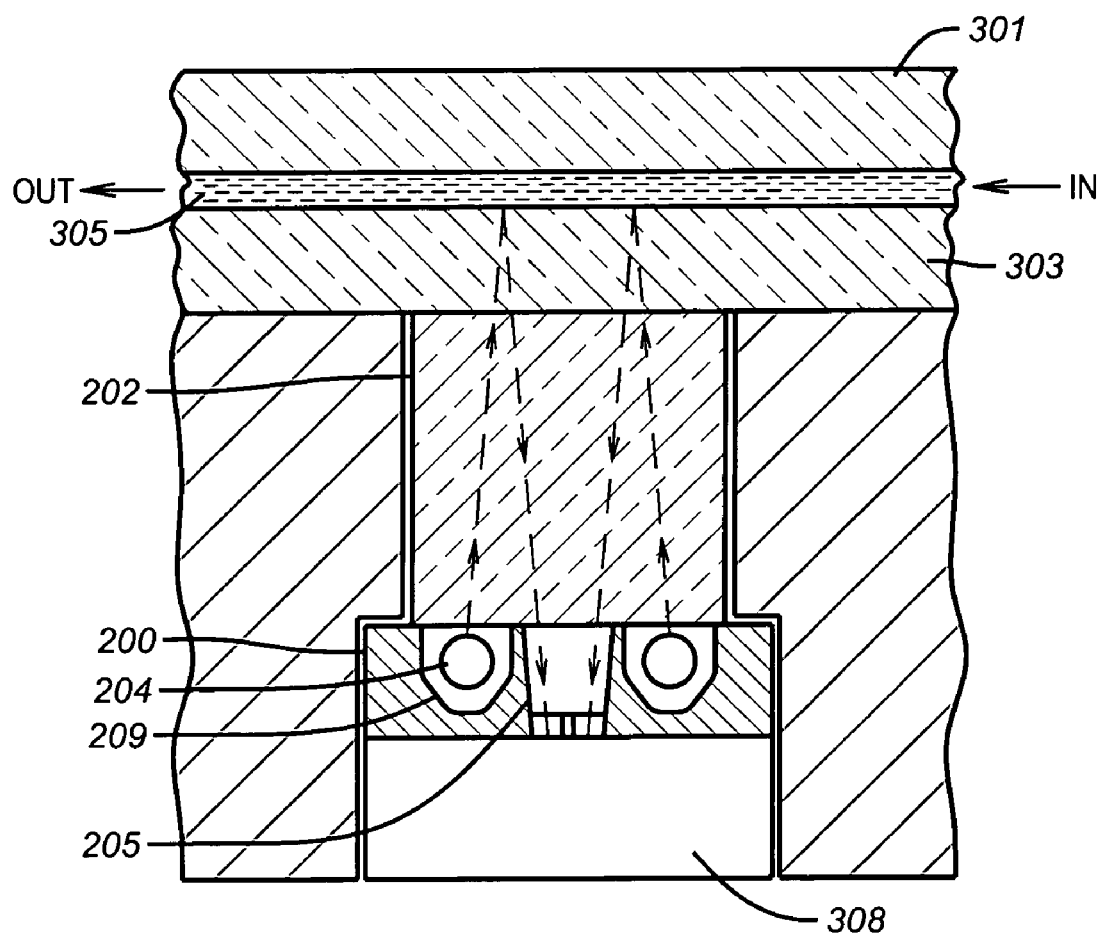
FIG. 3 is a diagram showing installation of the components from FIG. 2.

FIG. 3 illustrates an installation of the components from FIGS. 2A–C. The optically clear UV coupler 202, the UV bulbs 204, the base plate 200, the UV reflection channel 205 are assembled as in FIG. 2. To one side of the optically clear UV coupler 202 lies the UV bulbs 204, and to the opposite side and resting against it is a fluid containment system comprising two optically clear pressure containment plates, 301 and 303, which are capable of withstanding the high pressure of the formation fluid 305 flowing between them. In a preferred embodiment these containment plates are made of sapphire. The UV coupler 202 and the containment plates are of the materials having substantially the same refractive index, e.g., sapphire, so light can pass from one material to the other without deflection.

Voltage is applied to the bulbs 204 by the high voltage UV power supply shown in FIGS. 2A–C. Both the direct light from the UV bulbs 204 and the UV light reflected from the UV reflectors 209 are very effectively conveyed to the nearest portion of the formation fluid 305. To concentrate enough UV light on the sapphire window/crude interface, the invention comprises a faceted reflector mirror design 209 along the walls of the cavity of each miniature UV bulb and a light-pipe (the optically clear UV coupler) made of a high-refractive index material (sapphire) that captures a large solid angle of UV bulb's light and projects it forward. The reflector mirror improves light intensity by 25% and the light pipe improves light intensity by 235%. This light pipe also collects a large solid angle of the weak fluorescent light, which is forwarded to the detectors.

The formation fluid sample 305 fluoresces when exposed to the ultraviolet light source. The resulting fluorescent radiation from the fluid sample is conveyed back down through the rectangular hole 205 in the base plate and into a spectral analysis unit 308. The reflected fluorescent light provides useful information in the downhole analysis of the formation fluid. Spectral analysis unit 308 also hosts chemometric equations and a neural network for estimating formation fluid purity from fluorescent spectra measurements.

Implementing a UV fluorescence spectrometer downhole utilizes a miniature UV bulb fitting within a small space available within the existing tool. Temperature-dependent characteristics of the UV bulb affect the strike voltage. A higher strike (triggering) voltage is used to energize the UV bulb at elevated temperatures due to striking voltage "creep" with temperature. As an example, at 100° C., the UV lamp's first DC triggering voltage is 470 volts. As another example, at 150° C., a first triggering voltage is 720 volts, and at 175° C., it is 900 volts. Also, the shape of the striking pulse of the affects its magnitude. The required striking voltage is higher when the voltage undergoes a gradual rise in amplitude than when the striking voltage undergoes a sudden rise.

To eliminate this trigger-voltage creep with temperature, the present invention provides an alternating DC polarity voltage 207 for each successive trigger. Without reversing the DC polarity, with each successive trigger, the triggering voltage goes up a bit to the point where a tenth trigger at 175° C. reaches a triggering voltage of 1000 volts from its original 900 volts. Once triggered, the UV lamp operates between 150–160 volts and 4–5 milliamps. The operator either has to use a very high DC trigger voltage, alternate the DC trigger polarity, or go to an AC triggering and operating voltage.

In a preferred embodiment, the present invention provides for normalizing the fluorescence spectra which enables the present invention to counteract temperature-dependent behavior of the bulb. The UV bulb intensity drops to about half of its room temperature intensity value at 125° C. The present invention normalizes the fluorescence spectra to the brightness of the UV light bulb (which changes with temperature) by monitoring a red spectral line that is emitted in the spectrum of the UV bulb. The strength of this red line is proportional to the strength of the UV spectral line. The present invention enables an operator to use this red line as SampleView$^{SM}$ provides a red spectral channel, thereby enabling monitoring brightness of the U.V. source without the need for adding a separate UV detector.

In a preferred embodiment, the invention monitors crude-oil sample cleanup over time by examining the rising and leveling off of fluorescence over time. For wells drilled with synthetic hydrocarbon-based drilling mud, the invention monitors sample cleanup over time by monitoring fluorescence. The reason is that the base fluids for synthetic mud were designed to be environmentally friendly. Therefore, unlike crude oils, they do not contain the most common fluorescing hydrocarbon compounds, which are aromatics or poly-nuclear aromatics. The synthetic filtrate has little or no fluorescence. Thus, as the crude oil sample cleans up (less filtrate, more crude), the fluorescence increases.

In another embodiment, the invention estimates crude oil properties from fluorescence-ratio models, which are not sensitive to dilution by a generally non-fluorescing liquid, such as the filtrate of synthetic mud. For synthetic mud, whose filtrates have little, if any, fluorescence, the addition of filtrate to a crude oil acts as fluorescence diluents. The present invention provides models that correlate various crude oil properties (e.g., API, Nuclear Magnetic Resonance times T1 and T2, etc.) to ratios of the crude oil's fluorescence at two or more wavelengths. These ratio models are independent of the amount fluorescence-free synthetic mud-filtrate dilution provided that self-absorbance of the excitation and emission wavelengths is kept relatively small.

A processor 308 is provided for implementation of derived chemometric equations and a neural trained network for estimating sample properties from ultraviolet spectra measurements.

The present invention provides high-resolution spectral measurements that are much more accurate and also provides robust correlation equations for estimating the percentages of methane (natural gas), aromatics, olefins, saturates, and other crude oil properties through chemometrics or a neural network. These correlation equations are independent of the crude oil or filtrate involved.

In a preferred embodiment, the present invention uses chemometric derived equations or a neural network to determine the amount of aromatics, olefins, saturates and contaminants in a sample analyzed by the present invention based on spectral measurements. In known sampling techniques there is no direct measurement of a percent or level of contamination in a sample. The present invention provides a training set of known samples and utilizing chemometrics enables a computer to determine a mathematical expression for a percentage of aromatics, olefins, saturates and contaminants based on the spectrum measured for a sample. Using chemometrics eliminates a step in the process of determining the percent of aromatics, olefins, saturates and contaminants. Chemometrics also eliminates the need to know what each spectral peak represents and how much a particular peak overlaps another peak. For example, the present invention has been utilized to determine a percent of contaminants based on a chemometric formula derived from known sample having known percentages of aromatics, for example, samples containing 20, 30 and 50 percent aromatics. Typically filtrate does not contain aromatics, thus, the present invention enables direct determination of the percentage of contamination or filtrate in a sample. The training set can also be used to train a neural network to predict or determine the percent of aromatics, olefins, saturates and contaminants present in a sample. In a preferred embodiment the output of the chemometric calculation and the neural network are compared and a figure of merit value assigned to the output. When both outputs from the chemometric equation and the neural network agree, a high figure of merit of 1.0 is assigned. When the outputs disagree the outputs are averaged and a figure of merit equal to difference between the values divided by the sum of the values subtracted from 1.0 is assigned as a figure of merit.

The foregoing example of a preferred embodiment is intended for exemplary purposes only and is not intended to limit the scope of the invention, which is defined by the following claims.

What is claimed is:

1. A downhole tool for measuring fluorescence of a sample of formation fluid in a wellbore, comprising:
   a chamber containing a window having a first side in communication with the sample;
   an ultraviolet light source for illuminating the sample from a second side of the window;
   a source providing an alternating polarity striking voltage for each trigger of the light source; and
   a detector for measuring fluorescent spectra for the sample from the second side of the window.

2. The tool of claim 1, further comprising:
   a processor coupled to the detector including a figure of merit formula for calculating a figure of merit by subtracting from 1.0 the absolute value of the difference between two calculation components outputs.

3. The tool of claim 1, further comprising:
   a faceted mirror reflector to increase light intensity incident on the sample.

4. The tool of claim 1, wherein the window is made of sapphire.

5. The tool of claim 1, further comprising:
   a photo diode for monitoring the intensity of the ultra violet light source; and
   a normalizing component for adjusting measured fluorescent spectra to a change in the intensity of the ultra violet light source measured by the photo diode monitoring the intensity of the ultra violet light source.

6. The tool of claim 1, further comprising:
   a striking voltage pulse having a rise time of less than 500 milliseconds.

7. The tool of claim 1, further comprising:
   a neural network for determining a percentage of aromatics, olefins, saturates and contaminants present in the sample from two or more fluorescent channel measurements.

8. The tool of claim 1, further comprising:
   a chemometric calculation component for determining a percentage of at least one of aromatics, olefins, saturates and contaminants present in the sample from two or more fluorescent channel measurements.

9. The tool of claim 1, further comprising:
   a fluorescence ratio model for determining a percentage of aromatics, olefins, saturates and contaminants present in the sample from two or more fluorescent channel measurements.

10. The tool of claim 1, further comprising:
    calculation components comprising a neural network for determining a percentage of aromatics, olefins, saturates and contaminants present in the sample, a chemometric calculation component for determining a percentage of at least one of aromatics, olefins, saturates and contaminants present in the sample, a fluorescence ratio model for determining a percentage of aromatics, olefins, saturates and contaminants present in the sample; and
    a figure of merit component for comparing outputs from two of the calculation components and assigning a figure or merit to the calculation components outputs.

11. A method for down hole fluorescence spectrometry comprising:
placing a formation fluid in contact with a first site of a window of a chamber;
illuminating the formation fluid by an ultraviolet light source from a second side of the window of the chamber;
applying an alternating polarity striking voltage for each trigger of the light source; and
measuring fluorescent spectra for the formation fluid by a photo side from the second side of the window.

12. The method of claim 11, further comprising:
reflecting light at the UV light source; and
maximizing the WV light concentrated in an optical coupler to maximize light intensity incident on the formation fluid.

13. The method of claim 11, further comprising:
monitoring intensity of the ultra violet light source; and
normalizing measured fluorescent spectra to a change in intensity of the ultra violet light source.

14. The method of claim 11, further comprising:
applying a striking voltage pulse at a rise time of less than 500 milliseconds.

15. The method of claim 11, further comprising:
determining a percentage of aromatics, olefins, saturates and contaminants present in the sample from two or more fluorescent channel measurements utilizing a neural network.

16. The method of claim 11, further comprising:
determining in a chemometric calculation component for a percentage of at least one of aromatics, olefins, saturates and contaminants present in the sample from two or more fluorescent channel measurements.

17. The method of claim 11, further comprising:
determining in a fluorescence ratio model a percentage of aromatics, olefins, saturates and contaminants present in the sample from two or more fluorescent channel measurements.

18. The method of claim 11, further comprising:
determining a percentage of aromatics, olefins, saturates and contaminants present in the sample, in a chemometric calculation component for determining a percentage of at least one of aromatics, olefins, saturates and contaminants present in the sample, in a fluorescence ratio model for determining a percentage of aromatics, olefins, saturates and contaminants present in the sample; and
comparing outputs from two of the calculation components; and calculating a figure or merit for the calculation components outputs.

19. A downhole tool for measuring fluorescence of a sample of formation fluid in a weilbore, comprising:
a chamber receiving the sample;
a ultraviolet light source illuminating the sample;
a source providing an alternating polarity striking voltage for each trigger of the light source;
a detector measuring fluorescent spectra for the sample; and
a coupler optically coupling the ultraviolet light source and the detector to the sample.

20. The downhale tool of claim 19, further comprising a mirror projecting a light from the ultraviolet light source to the sample.

21. The downhole tool of 19, wherein the coupler is a light pipe.

22. The downhole tool of 19, wherein the chamber comprises a pair of pressure containment plates, the sample flowing therebetween.

23. The downhole tool of 19, further comprising a spectral analysis unit having at least one chemometric equation.

* * * * *